MULTI-GRATING ATTENUATOR FOR HIGH POWER PULSED LASER BEAMS

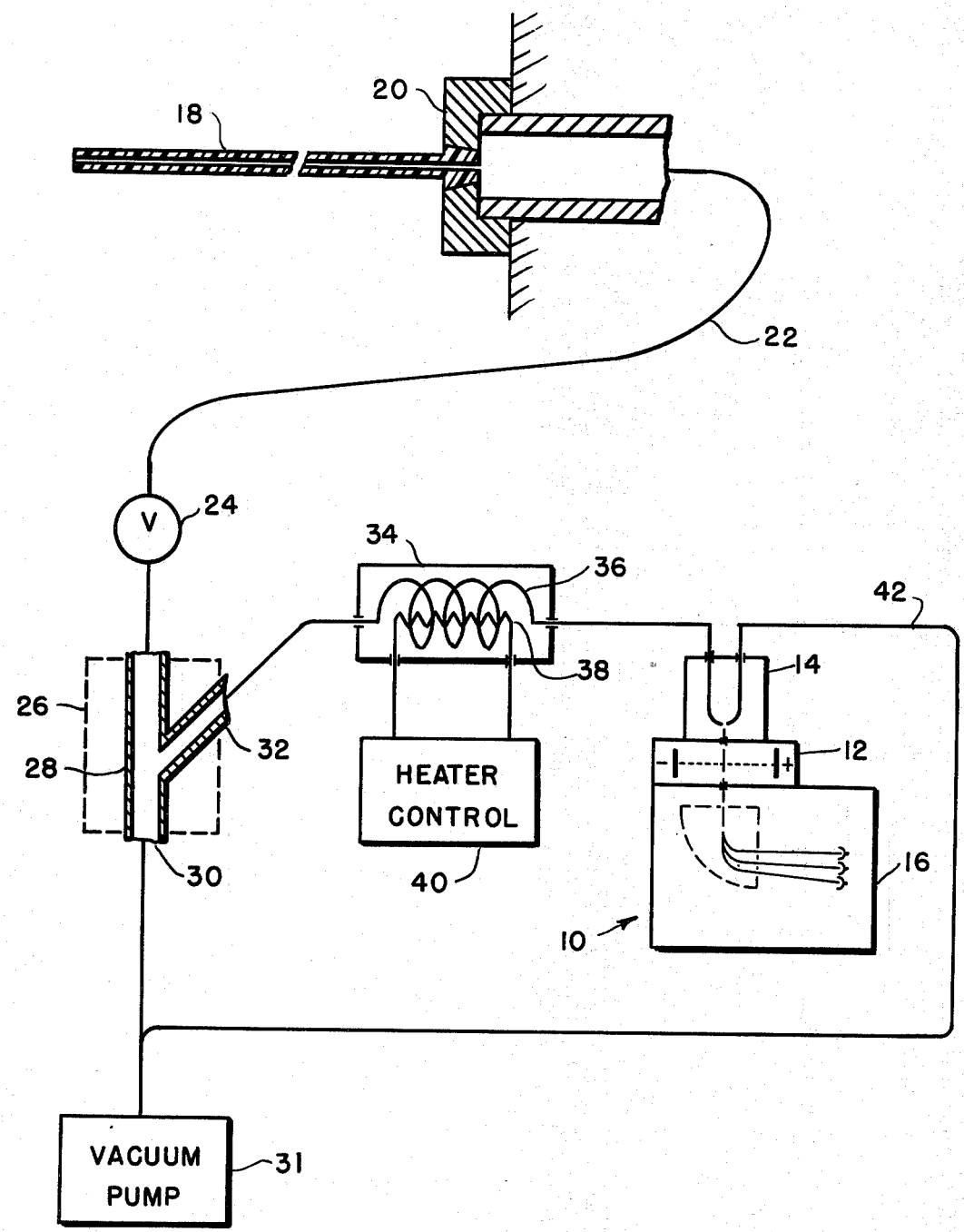

DEDICATORY CLAUSE

The invention described herein may be manufactured, used, and licensed by or for the Government for governmental purposes without the payment to us of any royalties thereon.

BACKGROUND OF THE INVENTION

To characterize the beam from a high power laser, it is necessary to isolate atmospheric distortions of the beam while operating the laser at full output power. To keep the transmitted beam intensity below the threshold for atmospheric disturbances, a hole grating or beam attenuator is used. These techniques are now well developed for this type of measurement and can be found in most textbooks on optics such as Principles of Optics by Max Born and Emit Wolf.

For high power cw lasers such as the GDL (gas dynamic lasers), a low transmission ($\approx 4\%$) cooled hole grating is used to attenuate the beam. For high power pulsed lasers operating in the single pulsed mode, a high transmission hole grating made from wires has been found to be useful. In this case the intensity distribution is measured in one of the higher orders of the diffraction patterns.

It is an object of this invention to supply a device which allows for the measurement of the intensity distribution of each pulse in the pulse train from a high power laser.

It is an additional object of this invention to supply a technique for positioning each grating in the laser beam at the appropriate time.

BRIEF DESCRIPTION OF THE DRAWINGS

FIG. 1 is a schematic illustration of the multi-grating attenuator for use with high power pulsed lasers.

FIG. 2 is a view of the attenuator disk of FIG. 1.

FIG. 3 is a diagrammatic plan view of the apparatus of FIG. 1 illustrating the diffracted beam of FIG. 1 used for diagnostic purposes. Only the disk and high powered laser of FIG. 1 is shown, for clarity.

DETAILED DESCRIPTION OF THE INVENTION

Referring to the drawing, in FIG. 1 the multi-grating attenuator 10 includes a disk 20 on which the wire gratings 22 are mounted; the disk is rotated by a motor 30 which is mounted on a stand 40. The RPM of the motor is adjusted so that a different grating is aligned with the laser beam from a high power pulsed laser 12 for each pulse. Thus if n gratings are used then each grating sees only 1/n of the pulses. During the time that a grating is not being used, it is allowed to cool or recover to its original condition before it is used again. To insure that each grating is in the proper position when the beam from the high power pulsed laser arrives, a small cw laser 14 such as a He-Ne laser is used to trigger the high power pulsed laser. The beam from the cw laser is blocked by the disc except when a small hole 24 in the disk passes the cw laser beam. This allows a pulse of light from the cw laser to initiate an electrical pulse generator 26 through a photodiode 28. The output of this electrical pulse generator is then used to fire or trigger the high power pulsed laser so that the high power laser beam arrives at the grating when it is in the proper location and passes therethrough to the test apparatus 32. For the test made with the A high power pulsed laser, the system delay was so short that the holes 24 in the disk were placed above the center of each grating. That is, the motion of the disk is neglibible during the time which elapsed between the cw laser beam leaving the disk and the high power pulse arriving at the grating. The gratings used are constructed from wires. With the use of these gratings, the intensity distribution in each order is the same and measurements of the beam quality may be made in a higher order where the power is low enough to allow for accurate work. Thus, one can know exactly what the beam looks like on the target 32 (neglecting thermal blooming and other nonlinear effects).

The diffraction order, n, where the beam diagnostics is located is not shown in FIG. 1 for clarity. FIG. 3 which is a diagrammatic view from the top of FIG. 1 illustrates the diffracted beam where the intensity is reduced slow enough for standard diagnostic techniques to be used. Such diagnostic device is designated by the numeral 33. The angle, $\theta$, at which the diagnostic beam leaves the grating is given by $\theta = \sin^{-1} n\lambda/d$ where $\lambda$ is the wavelength of the laser, d is the spacing between the wires, and n is the diffraction order.

This device can easily be calibrated with a cw laser if desired and, if desired, each grating may pass through a cooling bath after it has been exposed to the high power pulsed laser beam and then warm-air dried before being again exposed to the pulsed laser beam. In this manner a given size disk could be used at higher repetition rates without destroying the gratings.

Note that it is not necessary to attempt to synchronize the firing of the high power laser with the rotational speed of the disk since the technique used here synchronizes the high power laser pulse with each grating. Therefore, any variations in the rotational velocity of the disk will not cause the high power pulse to miss the grating and hit the disk.

An example calculation for ten gratings on a disk used to fire the high power pulsed laser at a rate of fifty pulses per second is as follows:

The angle $\lambda$ through which the disk must turn between pulses is $\alpha = s/r$ where s is the distance along an arc between the centers of two adjacent gratings and r is the radial distance out to the center of the gratings or for ten equally spaced gratings this will be $\alpha = 36°$. For fifty pulses per second $= 36°/0.02$ sec $= 1800$ degrees per second. Therefore, the disk would have to be rotated at 1800/360 or 5 RPS which is well within the range of currently available motors. By using faster motors or larger disks higher repetitive rates could be obtained.

The gratings need not be placed symetrically on the disk, thus providing for the production of pulses with unequal times between the pulses. That is this technique may be used to taylor the pulse train to the test requirements. It is also possible to decrease the up rate for a given disk and motor speed by simply covering some of the holes through which the cw laser beam passes.

The attenuation is varied by changing the wire size and/or wire spacing. This is accomplished in the lab by a simple jig.

The power in each order is a function of several variables and is not in a readily determined ratio. Therefore calibration with a cw laser is necessary when this technique is to be used to measure power per pulse using one of the higher orders.

RESPIRATORY GAS MOISTURE SEPARATOR SYSTEM FOR MASS SPECTROMETER MONITORING SYSTEMS

BRIEF SUMMARY OF THE INVENTION

In many modern large hospital facilities, the respiratory gases of patients, particularly those under intensive care, are continuously monitored and analyzed to provide advance warnings of possible respiratory difficulties. Various medical parameters, such as oxygen uptake, are conveniently and readily analyzed by the use of a medical mass spectrometer which continuously receives small samples of the combined gases, reduces the pressure through a molecular leak so that the combined gas molecules may be ionized by electron bombardment, and then subjects the ionized gas molecules to a magnetic field that segregates the various gas molecules according to their respective mass-to-charge ratios. Ion current collector cups are positioned to receive the ions from the particular gases of interest in the mixture and produce electrical currents proportional to the quantity of that gas admitted to the system.

Intensive care patients are often confined to a separate hospital ward where their respiratory gas constituents may be continually monitored by a centrally located medical mass spectrometer which may, in the larger hospitals, be located as much as one hundred feet or more from a monitored patient. The patient may breathe through a canula or a mouthpiece connected to a flowmeter that gives an indication of the amount of respiratory gas flow inhaled and exhaled by the patient. Connected to the flowmeter is a small capillary tube, normally having an inside diameter of approximately 0.020", which may be five or six feet in length to connect to a wall-mounted connection. The connection is the termination of a fifty to one hundred foot length of tubing having a larger diameter with corresponding lower flow resistance that leads to an appropriate distributor valve and thence to the medical mass spectrometer.

Normally, the respiratory gases exhaled by an intensive care patient have a very high moisture content. If these high moisture gases flow through the small relatively high resistance capillary tubing directly to the mass spectrometer, the warm moist gases will condense to form water droplets which, if permitted to enter into the very small spectrometer inlet leak, will cause the inlet and its associated tubing to be readily clogged, thus requiring repeated shutdown of the equipment to blow out condensed moisture.

The object of this invention is to remove that moisture from the conduit prior to the time it enters the medical mass spectrometer inlet leak.

Briefly described, the high moisture content of respiratory gases is reduced for medical mass spectrometer analysis by first rapidly reducing the pressure of the gas to hold the moisture in a vapor state and then directing the composite moist gas sample through a momentum separator in which the major part of the sample flows directly to an exhaust pump while a small sample for analysis is withdrawn through a reverse angle tee connection. This small gas sample, containing water vapor but with any heavier moisture droplets removed, is then passed through a heated section of the sample line maintained at about 100° C. before entering the spectrometer inlet leak.

BRIEF DESCRIPTION OF THE DRAWINGS

The single drawing is a schematic diagram illustrating the respiratory gas moisture separator of the invention.

DETAILED DESCRIPTION OF THE PREFERRED EMBODIMENT

Illustrated in the drawing is a typical medical mass spectrometer 10 such as described in U.S. Pat. No. 3,824,390 to Magyar. Spectrometer 10 includes an evacuated ionization chamber 12 through which an electron beam is passed to ionize gas molecules that are admitted to the chamber 12 from a sample inlet 14 which includes a conventional molecular leak, which, without disturbing the composition of the gas sample, reduces its pressure to a level compatible with the degree of vacuum provided in the chamber 12. The gas samples thus ionized are focused by an electrode and accelerated into an analyzing chamber 16 where the ionized gas molecules are subjected to a magnetic field that deflects the course of the ions into curved paths according to the respective mass-to-charge ratios of the various gas molecules therein. Collector cups, appropriately positioned within the analyzing chamber 16 to receive the deflected ions of each of the gases of interest, produce currents that are proportional to the quantity of the gas ions collected.

A very small quantity of gas is admitted into the chamber 12 through the inlet leak 14. It is, therefore, apparent that, if the gas sample contains impurities, such as moisture droplets, a very small inlet leak may readily become clogged, thereby requiring shutdown of the equipment for maintenance.

In hospital intensive care wards having facilities for monitoring the respiratory gasses of patients, the gas samples are generally withdrawn from a flowmeter which is connected to a breathing mouthpiece to measure the quantity of inhaled and exhaled gasses of the patient or withdrawn from other portions of the patient's breathing circuit. The flowmeter or breathing circuit includes a connector to which is connected a capillary tube, such as tube 18 in the drawings. Tube 18 normally has an inside diameter in the order of 0.020" and may have a length of approximately six feet to terminate in a wall connection 20. Also connected to the wall connection 20 is gas transmission tubing 22 which normally has a larger inside diameter of approximately 0.200" and a comparable lower flow resistance. The tubing dimensions are by way of example and other diameters may easily be employed. Tubing 22 extends from the wall connection 20 to an inlet valve 24 and thence to a momentum separator 26 illustrated in cross section detail in the drawing. Momentum separator 26 is comprised of a straight section of tubing 28 having a diameter substantially the same as that of the transmission tubing 22. The outlet 30 of the tubing 28 is connected to a vacuum pump 31 and the air sample to be analyzed is withdrawn through a tee connection 32 which is joined to the straight section 28 at an angle substantially greater than 90° from the outlet 30 so that flow into the connection 32 is substantially opposite to the flow of the main sample toward the vacuum pump 31. Therefore, as the moist gasses and condensed droplets are drawn rapidly through the straight section 28 by the vacuum pump 31, gas samples without the moisture droplets may be withdrawn through the tee connector 32.

Tee connector 32 is connected to a heat exchanger schematically illustrated as containing several coils of tubing 36 in a closed oven 34 heated by resistance elements 38 which, in turn, are controlled by a heater control 40. The heater control 40 maintains the temperature within the oven 34 at approximately 100° C. to further maintain the water in the sample in a vapor state. The sample is then carried into the inlet 14 of the mass spectrometer 10. The vacuum system (not shown) associated with the spectrometer 10 withdraws the necessary samples from the very small inlet leak and the unused gas sample then passes through the exhaust tubing 42 to the vacuum pump 31.

In operation, moist respiratory gases are admitted into the capillary tubing 18 from a patient's breathing circuit at atmospheric pressure. The capillary tubing 18 has a flow resistance that will drop the pressure at the wall connection 20 to a lower value, typically one-half atmosphere. The rapid pressure drop tends to keep all moisture in the vapor state even though the temperature also drops. This lower pressure gas is then transmitted through tubing 22 and valve 24 to the momentum separator 26 where any condensed moisture continues through to the vacuum pump 31 while the moist gas, without condensed droplets, passes through the tee connector 32 to the oven 34 before being admitted into the inlet leak 14 of the mass spectrometer 10. The moisture separating system therefore reduces the effect and quantity of water arriving at the inlet leak and permits accurate gas analysis without the repeated need to dry and clean the tubing that transmits the gases to the spectrometer.

What is claimed is:

1. A system for reducing moisture content of a respiratory gas sample drawn into a capillary tube for transmission to a medical mass spectrometer for analysis, said system comprising:

pressure dropping means for rapidly dropping the pressure of the respiratory gas sample in said capillary tube to maintain contained moisture in a vapor state;

a momentum moisture separator located in the transmission tubing between said pressure dropping means and the medical mass spectrometer, said separator having an inlet, an outlet, and a tee connection intercepting the gas flow between inlet and outlet at an acute angle to said flow; and heating means coupled between said separator tee connection and the inlet leak of said mass spectrometer.

2. The system claimed in claim 1 further including a vacuum pump coupled to the outlet of said momentum separator.

3. The system claimed in claim 2 wherein said pressure dropping means includes a connection between said capillary tube and a larger diameter transmission tubing connected between said capillary tube and the inlet of said separator.

4. The system claimed in claim 3 wherein said connection is a wall mounted connector.

5. The system claimed in claim 2 wherein said heating means comprises a heated coil of tubing between said separator tee connection and said spectrometer inlet, said coil being heated by electrical heating means.

6. The system claimed in claim 5 wherein said coil and said electrical heating means are enclosed in a heated chamber maintained at approximately 100° C.

7. The system claimed in claim 5 further including an inlet valve located in said gas transmission tubing between said wall connector and said separator inlet.

* * * * *